(12) United States Patent
Coupland et al.

(10) Patent No.: US 6,664,406 B1
(45) Date of Patent: Dec. 16, 2003

(54) NERVONIC ACID DERIVATIVES, THEIR PREPARATION AND USE

(75) Inventors: Keith Coupland, York (GB); Yann Raoul, North Humberside (GB)

(73) Assignee: Croda International PLC, North Humberside (GB)

( * ) Notice: Subject to any disclaimer, the term of this patent is extended or adjusted under 35 U.S.C. 154(b) by 0 days.

(21) Appl. No.: 10/130,672

(22) PCT Filed: Nov. 23, 2000

(86) PCT No.: PCT/GB00/04453
§ 371 (c)(1),
(2), (4) Date: Aug. 19, 2002

(87) PCT Pub. No.: WO01/38288
PCT Pub. Date: May 31, 2001

(30) Foreign Application Priority Data

Nov. 24, 1999 (GB) .............................. 9927629

(51) Int. Cl.[7] .............................. C07C 57/00
(52) U.S. Cl. ............... 554/225; 554/227; 554/159; 554/168; 514/558; 514/560; 514/825; 514/838; 514/861; 514/885; 514/886; 514/912; 514/894
(58) Field of Search ................ 589/159, 168, 589/227; 514/558, 828, 838, 861, 888, 884, 912

(56) References Cited

U.S. PATENT DOCUMENTS 5,194,448 A    3/1993   Coupland et al.

FOREIGN PATENT DOCUMENTS

| WO | 9107955 | 6/1991 |
| WO | 9634846 | 11/1996 |
| WO | wo-96/34846 | * 11/1996 |

OTHER PUBLICATIONS

European Search Report.
Great Britain Search Report.

* cited by examiner

*Primary Examiner*—Deborah Carr
(74) *Attorney, Agent, or Firm*—Stevens, Davis, Miller & Mosher, L.L.P.

(57) ABSTRACT

The present invention relates to a nervonic acid derivatives of formula (I)

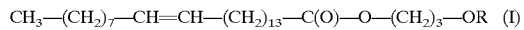

$$CH_3-(CH_2)_7-CH=CH-(CH_2)_{13}-C(O)-O-(CH_2)_3-OR \quad (I)$$

wherein R is hydrogen (H) or a residue of a carboxylic acid; or a salt of the compound where R is H; or a bioprecursor, prodrug thereof. Those compounds wherein R is other than H have pharmacological activity, in particular anti-inflammatory and immunomodulatory effects. Those compounds wherein R is H can be used to prepare the pharmacologically active derivatives.

29 Claims, No Drawings

NERVONIC ACID DERIVATIVES, THEIR PREPARATION AND USE

This application is a 371 of PCT/GB00/04453 filed Nov. 23, 2000.

The present invention relates to certain fatty acid esters and their preparation, and to the use of such compounds or pharmaceutical formulations thereof in medicine in a mammal, including man, as, for example, anti-inflammatory or immunomodulatory agents.

Fatty acids are generally known to include the carboxylic acids that make up glycerides, such as triacylglycerols, the carboxylic esters comprised in the fat storage cells of plants and animals. Many such fatty acids are straight-chain compounds, having from three to eighteen carbon atoms ($C_3$–$C_{18}$); except for the $C_3$ and $C_5$ compounds, only acids containing an even number of carbon atoms are present in substantial amounts, due to their biosynthesis. There are both saturated and unsaturated fatty acids, such as the unsaturated $C_{18}$ oleic, α-linoleic and γ-linolenic (GLA) fatty acids, each having one, two and three carbon-carbon double bonds, respectively. Conventional notation therefore refers to these acids as 18:1, 18:2 and 18:3 fatty acids, respectively. The configuration about these double bonds is usually cis, which lowers the melting point of the corresponding fat (compared to the corresponding saturated and trans compounds).

Besides these short- and medium-chain fatty acids, those with longer chains, such as $C_{16}$–$C_{24}$, are also known and have been investigated, particularly those available from fish oils, such as eicosapentaenoic (EPA, 20:5 (n–3)) and docosahexaenoic (DHA, 22:6 (n–3)) acids, where, in (n–x), x indicates the position of the first carbon-carbon double bond with respect to the terminal methyl group on the fatty acid.

As well as their dietary metabolism and their potential dietary use, some fatty acids have been investigated in relation to medical conditions such as schizophrenia (GLA and DHA) and bipolar disorder (EPA and DHA). Some have also been proposed for improving the transport of biologically active drugs ('bioactives') across lipid membranes by linking the bioactive either directly or indirectly to certain fatty acids. For example, in PCT patent specification no. WO 96/34846, it is disclosed that any of the essential fatty acids (which include GLA, DHA and EPA) or any other $C_{12-30}$ fatty acid having at least two carbon-carbon double bonds may be so used. Amongst a wide range of possible bioactives and (12–30:≧2) fatty acids mentioned in that specification is specifically disclosed GLA-GLA, being a pair of GLA molecules linked via a propane-1,3-diol moiety, namely 1,3-(di-z,z,z,-octadeca-6,9,12-trienoyloxy)propane. However, no biological results in any pharmacological tests are shown for GLA-GLA, other than a report that it was administered to rats and mice up to 10 g/kg without evidence of diarrhea (ie absence of toxicity, rather than presence of therapeutic effect).

Nevertheless, GLA-GLA is mentioned as one possible propane-1,3-diol compound having a broad range of listed uses, including the treatment of inflammatory diseases. However, as reported hereinbelow with particular reference to Example 4, we found that GLA:GLA had no effect in our tests for anti-inflammatory activity. Accordingly, it might be expected that other combinations of (12–30:≧2) fatty acids linked via a propane-1,3-diol moiety might also not show anti-inflammatory action, especially where such action was not already demonstrated for at least one of the fatty acid moieties involved.

Furthermore, no possibility of using other types of fatty acids, such as those having only one carbon-carbon double bond, is contemplated in WO 96/34846. One such different type of fatty acid is nervonic acid. Nervonic acid (24:1 (n–9)) is cis (or z)-tetracos-15-enoic acid; it is not classed as an essential fatty acid and has only one unsaturated C═C bond. It plays a part in the biosynthesis of myelin and is one of the major fatty acids in brain sphingolipids. Nervonic acid has therefore been implicated in diseases involving demyelination, such as adrenoleukodystrophy (ALD) and multiple sclerosis (MS). It has therefore been proposed to administer nervonic acid or a source thereof as a pharmaceutical formulation thereof to patients suffering from demyelinating conditions (as described in PCT published specification no. WO 91/07955), or to provide nervonic acid or a functional derivative thereof as a dietary supplement, for example, as baby or infant feeds, or to pregnant or lactating women (as described in PCT published specification no PCT/GB95/01985). Although the precise causes of MS are not yet known, strong evidence now suggests that MS results from an autoimmune process triggered by an environmental factor, possibly a non-specific viral infection, in a genetically susceptible individual, in which immune cells mistake myelin as a foreign invader and attack it. This process produces perivascular inflammation in the CNS and eventually damages not only myelin but also underlying nerve tissue. However, nervonic acid is not known to have any general effect on inflammation or inflammatory diseases.

As a result of damage to the myelin and nerve tissue, the blood-brain barrier is disrupted, enabling activated T-cells to enter the brain and recruit other lymphocytes. Activated T-cells release lymphotoxin, interferon gamma (IFN-γ) and other inflammatory cytokines. Lymphotoxin can damage oligodendrocytes, and IFN-γ, which has been shown to provoke MS exacerbations, stimulates the immune system in a number of ways thought to aggravate MS. Oligodendrocyte cells synthesise myelin-specific proteins and lipids, and their role is critical for both normal myelin sheath formation and normal brain function.

For example, IFN-γ augments expression of major histocompatibility complex (MHC) class II molecules on macrophages, and induces their expression on astrocytes, microglia and endothelial cells. Antigenic myelin peptides associated with these MHC molecules are recognised by T-cells, which proliferate in response to antigen presentation, amplifying the immune response.

Macrophages activated by IFN-γ also release tumour necrosis factor (TNF), which has been shown to damage oligodendrocytes in vitro. In addition, cytokines, proteinases and lipases are secreted, and B-cells are induced to synthesise antibodies. This response results in demyelination and gliosis, which causes nerve impulses to be slowed or halted and produces the symptoms of MS.

It has now surprisingly been found that certain derivatives of nervonic acid possess anti-inflammatory and/or immunomodulatory activity. Furthermore, some of these derivatives assist in the passage of nervonic acid across the blood-brain barrier.

Accordingly, the present invention provides a compound of formula (I):

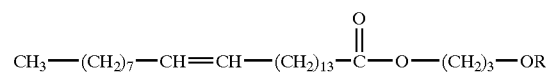

(I)

wherein R is hydrogen (H) or a residue of a carboxylic acid or a salt of the compounds where R is H.

The definition of formula (I) also includes, where applicable, individual isomers and mixtures thereof; and derivatives (especially bioprecursors or pro-drugs) thereof.

The term "bioprecursor" or "pro-drug" means a pharmacologically acceptable derivative—eg an ester (such as a biolabile ester derivative of a —COOH group)—that is converted in vivo to a compound of the present invention. Suitable pro-drugs can be determined by reference to Goodman and Gilman, The Pharmacological Basis of Therapeutics, 8th Edition, McGraw-Hill, Int. Ed. 1992, particularly "Biotransformation of Drugs", pp. 13–15.

The carboxylic acid referred to in the definition of R preferably has from 1 to 26 carbon atoms, and may be straight- or branched-chain, saturated or unsaturated. More preferably, the carboxylic acid is straight chain and is selected from the group consisting of mono- and poly-unsaturated fatty acids. Particularly preferred are compounds of formula (I) wherein R is a residue of a $C_{18}$ to $C_{24}$ mono- or poly-unsaturated fatty acid, having from 1 to 6 carbon-carbon double bonds. Especially preferred is when R is a residue of nervonic acid (24:1(n–9)), docosahexaenoic acid (22:6(n–3)) or γ-linolenic acid (18:3(n–6)), where x in (n–x) indicates the position of the first double bond with respect to the terminal methyl group of the fatty acid.

It will be understood by the person skilled in the art that the compounds of formula (I) wherein R is H are useful as intermediates in the synthesis of other compounds of formula (I). Accordingly, the present invention provides a method for the preparation of the compounds of formula (I) wherein R is a residue of a carboxylic acid, which method comprises reacting the compound of formula (IA), namely, 1-(z-15-tetracosenoyloxy)-3-hydroxypropane:

(IA)

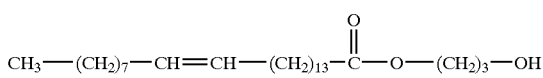

with the corresponding carboxylic acid of formula R—H, wherein R is as defined for formula (I).

Suitable conditions for this esterification reaction are known to those skilled in the art and include the presence of hypophosphorous acid, preferably with heating to reflux under an inert atmosphere, such as nitrogen.

The compound of formula (IA) may itself be prepared in conventional manner, such as from the reaction of the acid chloride of nervonic acid (ie $CH_3$—$(CH_2)_7$—CH=CH—$(CH_2)_{13}$—COCl) with propane-1,3-diol in the presence of a base, such as an organic base, for example, trialkylamines eg triethylamine and tributylamine, and pyridine, 2,6-dimethylpyridine and quinoline, preferably in an organic aprotic solvent, such as a halogenated alkane, for example, dichloromethane, ether, tetrahydrofuran and toluene. The reaction is preferably carried out with cooling, such as to about 0° C., under an inert atmosphere, such as nitrogen.

The acid chloride of nervonic acid (z-15-tetracosenoyl chloride) can be prepared in conventional manner from nervonic acid and thionylchloride, phosphorous trichloride or, especially, phosphorous pentachloride, preferably in a polar solvent such as an ether in anhydrous conditions and preferably under an inert atmosphere.

In the case of the preparation of the compound of formula (I) wherein R is the residue of nervonic acid, the two-step process described above can be carried out in a single pot from nervonic acid, propane-1,3-diol and, for example, hypophosphorous acid.

Nervonic acid is commercially-available from Aldrich Chemicals, UK or is otherwise available as described, for example, in U.S. patent specification no. U.S. Pat. No. 5,194,448 or published PCT patent specification no. PCT/GB95/01985.

The compounds of formula (I) wherein R is other than H, namely, compounds of formula (IB):

(IB)

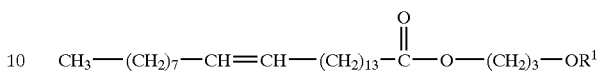

wherein $R^1$ is a residue of a carboxylic acid have, as mentioned before, surprisingly been found to possess anti-inflammatory and/or immunomodulatory activity.

Preferred carboxylic acid residues are as described hereinabove with respect to the definition of R.

Accordingly, the present invention provides the following specific compounds of formula (IB):

1-(z-15-tetracosenoyloxy)-3-(z,z,z-6,9,12-octadecatrienoyloxy)propane (hereinafter referred to as NA:GLA);

1-(z-15-tetracosenoyloxy)-3-(z-4,7,10,13,16,19-docosahexaenoyloxy)propane (hereinafter referred to as NA:DHA); and 1,3-di-(z-15-tetracosenoyloxy)propane (hereinafter referred to as NA:NA).

By 'anti-inflammatory' herein is meant the ability to reduce, ameliorate or prevent inflammation or an inflammatory response. By 'immunomodulatory' herein is meant the ability to modulate an immune response, such as by suppressing or stimulating such a response. It will be understood by those skilled in the art that both anti-inflammatory and immunomodulatory activity may be desirable for the treatment or prevention of some medical conditions.

The anti-inflammatory and/or immunomodulatory effects of the compounds of formula (IB) can be observed in the experimental allergic encephaolmyelitis (EAE) tests described in more detail hereinbelow in the Examples. EAE is an autoimmune inflammatory disease of the CNS characterised by perivascular and subpial inflammatory infiltrates and lesions of demyelination. It can be induced by immunisation with whole homogenised spinal cord or brain material, purified myelin or oligodendrocytes, purified components of myelin, combined with adjuvants. The use of adjuvants, such as Freund's adjuvant, is necessary to enhance the immunological response that ultimately results in disease. Due to the relative ease of purification, myelin basic protein (MBP) and proteolipid protein (PLP), and their fragments, have been studied extensively as encephalitogens in EAE.

EAE models may be broadly classified as acute monophasic EAE or chronic relapsing EAE:

In acute EAE, susceptible animals injected with small doses of myelin antigens in complete Freund's adjuvant (CFA) succumb to paralytic disease within 10 to 14 days. The onset of disease is observed as loss of tone of the tail and/or mild paralysis of the hind feet, progressing to muscle wasting in the haunches and lower back. In severe cases, paralysis may spread to the forelimbs. If the animals do not become moribund, the severity of paralysis decreases and the animals recover. Classic acute EAE can be observed in Lewis rats; such models are ideal to study the effects of drug and/or immunotherapy aimed at reducing acute CNS inflammation.

The clinical grading and classification of neurological deficit depends on the strain of animal used and the course of the disease. A 0 to 6 point grading is generally used, ranging from asymptomatic (0) to death (6).

Prior to onset of clinical signs, animals lose weight, and examination of the CNS reveals mononuclear cell infiltration, particularly in the spinal cord. Following the onset of clinical signs, increasing numbers of mononuclear cells infiltrate the CNS and accumulate in the subpial areas of the spinal cord prior to infiltration of the parenchyma. Immunohistochemistry and cell isolation techniques have identified the predominant cells as macrophages and CD4+ T cells. It is noteworthy that demyelination is not a classic sign of acute EAE, and therefore this test is indicative of anti-inflammatory/immunomodulatory activity in general, rather than only of that which might accompany demyelinating diseases.

Chronic EAE is characterised by a continuation of neurological deficit without recovery, following an episode of acute EAE.

Alternatively, full recovery (remission) occurs after the acute phase, which is followed by phases of clinical and histological disease and further remissions. This is chronic relapsing (and remitting) EAE, which is more closely resembling of multiple sclerosis symptoms than the acute model. Although chronic relapsing EAE has been characterised in many species, mouse models have the advantage of a well-characterised immune system and the availability of a wide range of immunological reagents with which to probe the disease.

In addition to the inflammatory effects existing with EAE, chronic relapsing EAE (CREAE) presents primary demyelination in these inflammatory areas, particularly pronounced in a relapse phase.

The very positive results obtained in the acute EAE tests with NA:NA demonstrate that the use of the propane-1,3-diol moiety as a linker between the two fatty acyl moieties is of major importance, since glyceryl trinervonate (GTN), which consists of three fatty acyl moieties bound to a glycerol backbone, did not show any effect on the course of acute EAE. However, it is not enough to assume that the mere presence of the propane-1,3-diol moiety is itself sufficient to give rise to positive results. We have found that NA:GLA also gave rise to positive results, whereas tests using GLA:GLA showed absence of effect. This is surprising, since the disclosure of PCT patent specification no. WO 96/34846, discussed above, might lead to the expectation that GLA:GLA would give particularly beneficial biological results. Simply linking together two fatty acid moieties ($R^1$) via a propane-1,3-diol moiety therefore does not necessarily result in a compound having immunomodulatory and/or anti-inflammatory activity.

Therefore, propane-1,3-diol derivatives of nervonic acid would seem to have unpredictable and differing activities compared to those of fatty acids having two or more unsaturated C=C bonds. A structure-activity relationship for NA:NA has been established and it has also been shown that nervonic acid, in the form of the derivatives NA:NA and NA:GLA, shows general anti-inflammatory activity, which has not been shown before.

Accordingly, the compounds of formula (IB) may be used in the relief of rheumatoid arthritis, rheumatoid spondylitis, osteroarthritis, gouty arthritis and other arthritic conditions; inflamed joints; eczema and other inflammatory skin conditions; inflammatory eye conditions including conjunctivitis; pyresis and other conditions associated with inflammation, including the reduction of tissue necrosis in chronic inflammation, the suppression of tissue rejection following transplant surgery, Crohn's disease and ulcerative colitis.

The compounds of formula (IB) may also be used in the treatment or prophylaxis of airway inflammatory conditions such as asthma and bronchitis. Other conditions, which are suitable for treatment by an immunomodulator, include systemic lupus erythematosis; multiple sclerosis; myasthenia gravis; progressive systemic sclerosis; atopic dermatitis; hyperimmunoglobin E; hepatitis B antigen negative chronic active hepatitis; Hashimoto's thyroiditis; familial Mediterranean fever; Grave's disease; autoimmune haemolytic anaemia; primary biliary cirrhosis; and inflammatory bowel disease. Further conditions, suitable for treatment by an immunostimulant, include any wherein the immune system is compromised, disabled or dysfunctional, such as in AIDS patients, and those associated with viral infections, such as HIV.

Preferred compounds of formula (IB) for use as an anti-inflammatory and/or immunosuppressant include NA:NA and NA:GLA, especially, NA:GLA; preferred for immunostimulant use is NA:DHA.

The amount required of a compound of formula (IB) (the active ingredient) for therapeutic effect will, of course, vary both with the particular compound, the route of administration and the mammal under treatment. A suitable dose of a compound of formula (IB) for a mammal suffering from a condition as defined hereinbefore is in the range of from 0.1 to 1000 mg of base per kilogram body weight, the most preferred dosage being 0.5 to 500 mg/kg of mammal body weight, such as from 1 to 50 mg/kg, for example 5 to 25 mg/kg; administered two or three times daily.

In the case of the treatment or prophylaxis of inflammatory airway conditions, a suitable anti-asthmatic dose of a compound of formula (IB) is 1 mg to 10 mg of base per kilogram body weight, the most preferred dosage being 1 mg to 5 mg/kg of mammal body weight, for example from 1 to 2 mg/kg.

While it is possible for an active ingredient to be administered alone as the raw chemical, it is preferable to present it as a pharmaceutical formulation. The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulation and not deleterious to the recipient thereof.

Conveniently, the active ingredient comprises from 0.1% to 99.9% by weight of the formulation. Suitably, unit doses of a formulation contain between 0.1 mg and 1 g of the active ingredient. Preferably, the formulation is suitable for administration from one to six, such as two to four, times per day. For topical administration, the active ingredient preferably comprises from 1% to 2% by weight of the formulation but the active ingredient may comprise as much as 10% w/w. Formulations suitable for nasal or buccal administration, such as the self-propelling powder-dispensing formulations described hereinafter, may comprise 0.1 to 20% w/w, for example about 2% w/w of active ingredient.

The formulations include those in a form suitable for oral, ophthalmic, rectal, parenteral (including subcutaneous, vaginal, intraperitoneal, intramuscular and intravenous), intra-articular, topical, nasal or buccal administration.

The formulations may conveniently be presented in unit dosage form and may be prepared by any of the methods well known in the art of pharmacy. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be in the form of a bolus, electuary or paste. For such formulations, a range of dilutions of the active ingredient in the vehicle is suitable, such as from 1% to 99%, preferably 5% to 50% and more preferably 10% to 25% dilution. Depending upon the level of dilution, the formulation will be either a liquid at room temperature (in the region of about 20° C.) or a low-melting solid. For example, compositions where NA:GLA is the active ingredient are miscible in all proportions at room temperature, whereas those comprising NA:NA are liquids at room temperature when the concentration is at or below about 25%.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert diluent.

Formulations for rectal administration may be in the form of a suppository incorporating the active ingredient and a carrier such as cocoa butter, or in the form of an enema.

Formulations suitable for parenteral administration comprise a solution, suspension or emulsion, as described above, conveniently a sterile aqueous preparation of the active ingredient that is preferably isotonic with the blood of the recipient.

Formulations suitable for intra-articular administration may be in the form of a sterile aqueous preparation of the active ingredient, which may be in a microcrystalline form, for example, in the form of an aqueous microcrystalline suspension or as a micellar dispersion or suspension. Liposomal formulations or biodegradable polymer systems may also be used to present the active ingredient particularly for both intra-articular and ophthalmic administration.

Formulations suitable for topical administration include liquid or semi-liquid preparations such as liniments, lotions or applications; oil-in-water or water-in-oil emulsions such as creams, ointments or pastes; or solutions or suspensions such as drops. For example, for ophthalmic administration, the active ingredient may be presented in the form of aqueous eye drops, as for example, a 0.1–1.0% solution.

Drops according to the present invention may comprise sterile aqueous or oily solutions and may be prepared by dissolving the active ingredient in a suitable aqueous solution containing a bactericide and/or fungicidal agent and/or any other suitable preservative. The resulting solution may then be clarified by filtration, transferred to a suitable container, and then sealed and sterilised by autoclaving or maintaining at 90–100° C. for half an hour. The solution may be sterilised by filtration and transferred to the container by an aseptic technique. Preservatives, bactericidal and fungicidal agents suitable for inclusion in the drops are phenylmercuric salts (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the eye. An eye lotion may comprise a sterile aqueous solution optionally containing a bactericide or preservative prepared by methods similar to those for the preparation of drops. Lotions or liniments for application to the skin may also include an agent to hasten drying and to cool the skin, such as an alcohol, or a softener or moisturiser such as glycerol or an oil such as castor oil or arachis oil.

Creams, ointments or pastes according to the present invention are semi-solid formulations of the active ingredient for external application. They may be made by mixing the active ingredient in granule or powdered form, alone or in solution or suspension in an aqueous or non-aqueous solution in suitable machinery, with a greasy or non-greasy basis. The basis may comprise one or more of a hard, soft or liquid paraffin, glycerol, beeswax, a metallic soap; a mucilage; an oil such as a vegetable oil, eg almond, corn, arachis, castor or olive oil; wool fat or its derivatives; or a fatty acid ester of a fatty acid together with an alcohol such as propylene glycol or macrogols. The formulation may also comprise a suitable surface-active agent, such as an anionic, cationic or non-ionic surfactant such as a glycol or polyoxyethylene derivatives thereof. Suspending agents such as natural gums may be incorporated, optionally with other inorganic materials, such as silicaceous silicas, and other ingredients such as lanolin.

Formulations suitable for administration to the nose or buccal cavity include those suitable for inhalation or insufflation, and include powder, self-propelling and spray formulations such as aerosols and atomisers. The formulations, when dispersed, preferably have a particle size in the range of 10 to 200µ.

Such formulations may be in the form of a finely comminuted powder for pulmonary administration from a powder inhalation device or self-propelling powder-dispensing formulations, where the active ingredient, as a finely comminuted powder, may comprise up to 99.9% w/w of the formulation. In the case of self-propelling solution and spray formulations, the effect may be achieved either by choice of a valve having the desired spray characteristics (ie being capable of producing a spray having the desired particle size) or by incorporating the active ingredient as a suspended powder of controlled particle size. Thus the formulation, instead of passing into the lungs, is largely retained in the nasal cavity. These self-propelling formulations may be either powder-dispensing formulations or formulations dispensing the active ingredient as droplets of a solution or suspension.

Self-propelling powder-dispensing formulations preferably comprise dispersed particles of solid active ingredient, and a liquid propellant having a boiling point of below 18° C. at atmospheric pressure. The liquid propellant may be any propellant known to be suitable for medicinal administration and may comprise one or more lower alkyl hydrocarbons or halogenated lower alkyl hydrocarbons or mixtures thereof; chlorinated and fluorinated lower alkyl hydrocarbons are especially preferred. Generally, the propellant constitutes 50 to 99.9% w/w of the formulation whilst the active ingredient constitutes 0.1 to 20% w/w, for example, about 2% w/w, of the formulation.

The pharmaceutically acceptable carrier in such self-propelling formulations may include other constituents in addition to the propellant, in particular a surfactant or a solid diluent or both. Surfactants are desirable since they prevent agglomeration of the particles of active ingredient and maintain the active ingredient in suspension. Especially valuable are liquid non-ionic surfactants and solid anionic surfactants or mixtures thereof. Suitable liquid non-ionic surfactants are those having a hydrophile-lipophile balance (HLB, see Journal of the Society of Cosmetic Chemists Vol. 1 pp. 311–326 (1949)) of below 10, in particular esters and partial esters of fatty acids with aliphatic polyhydric alcohols, for instance, sorbitan mono-oleate and sorbitan trioleate, available commercially as 'Span 80' (Trade Name) and 'Span 85' (Trade Name), respectively. The liquid non-ionic surfactant may constitute from 0.01 up to 20% w/w of the formulation, though preferably it constitutes below 1% w/w of the formulation. Suitable solid anionic surfactants include alkali metal, ammonium and amine salts of dialkyl sulphosuccinate (where the alkyl groups have 4 to 12 carbon atoms) and alkyl benzene sulphonic acid (where the alkyl group has 8 to 14 carbon atoms). The solid anionic surfactants may constitute from 0.01 up to 20% w/w of the formulation, though preferably below 1% w/w of the composition. Solid diluents may be advantageously incorporated in such self-propelling formulations where the density of the active ingredient differs substantially from the density of the propellant; also, they help to maintain the active ingredient in suspension. The solid diluent is in the form of a fine powder, preferably having a particle size of the same order as that of the particles of the active ingredient. Suitable solid diluents include sodium chloride, sodium sulphate and sugars.

Formulations of the present invention may also be in the form of a self-propelling formulation wherein the active ingredient is present in solution. Such self-propelling formulations may comprise the active ingredient, propellant and co-solvent, and advantageously an antioxidant stabiliser. The propellant is one or more of these already cited above. Co-solvents are chosen for their solubility in the propellant, their ability to dissolve the active ingredient, and for their having the lowest boiling point consistent with these above-mentioned properties. Suitable co-solvents are lower alkyl alcohols and mixtures thereof. The co-solvent may constitute 5 to 40% w/w of the formulation, though preferably less than 20% w/w of the formulation. Antioxidant stabilisers may be incorporated in such solution-formulations to inhibit deterioration of the active ingredient and are conveniently alkali metal ascorbates or bisulphites. They are preferably present in an amount of up to 0.25% w/w of the formulation.

Such self-propelling formulations may be prepared by any method known in the art. For example, the active ingredient (either as particles as described hereinbefore in suspension in a suitable liquid or in up to 20% w/w solution in an acceptable co-solvent, as appropriate) is mixed with any other constituents of the pharmaceutically acceptable carrier. The resulting mixture is cooled, introduced into a suitable cooled container and propellant is added thereto in liquid form; and the container is sealed. Alternatively, such self-propelling formulations may be prepared by mixing the active ingredient either in particles as hereinbefore described or in 2 to 20% w/w alcohol or aqueous solution as appropriate, together with the remaining constituents of the pharmaceutically acceptable carrier other than the propellant; introducing the resulting mixture, optionally with some propellant, into a suitable container; and injecting the propellant, under pressure, into the container at ambient temperature through a valve which comprises a part of the container and is used to control release of the formulation from it. Desirably, the container is purged by removing air from it at a convenient stage in the preparation of the self-propelling formulation.

A suitable container for a self-propelling formulation is one provided with a manually operable valve and constructed of aluminium, stainless steel or reinforced glass. The valve should, of course, be one having the desired spray characteristics of particle that which delivers a fixed amount of the formulation on the occasion of each operation of the valve, for example, about 50 to 100 microliters of formulation in each delivery; metered-dose devices are well known to those skilled in the art.

Formulations of the present invention may also be in the form of an aqueous or dilute alcoholic solution, optionally a sterile solution, of the active ingredient for use in a nebuliser or atomiser, wherein an accelerated air stream is used to produce a fine mist consisting of small droplets of the solution. Such formulations usually contain a flavouring agent such as saccharin sodium and a volatile oil. A buffering agent such as sodium metabisulphite and a surface active agent may also be included in such a formulation which should also contain a preservative such as methylhydroxybenzoate.

Other formulations suitable for nasal administration include a powder, having a particle size of 20 to 500 microns, which is administered in the manner in which snuff is taken, ie by rapid inhalation through the nasal passage from a container of the powder held close up to the nose.

In addition to the aforementioned ingredients, the formulations of this invention may include one or more additional ingredients such as diluents, buffers, flavouring agents, binders, surface active agents, thickeners, lubricants, preservatives eg methylhydroxybenzoate (including anti-oxidants), emulsifying agents and the like. A particularly preferred carrier or diluent for use in the formulations of this invention is a lower alkyl ester of a $C_{18}$ to $C_{24}$ mono-unsaturated fatty acid, such as oleic acid, for example ethyl oleate. Other suitable carriers or diluents include capric or caprylic esters or triglycerides, or mixtures thereof, such as those caprylic/capric triglycerides sold under the trade name Miglyol, eg Miglyol 810.

Any other therapeutic ingredient may comprise one or more of the following: antibiotic, antifungal and antiviral agents.

According to the present invention there are therefore provided:

(a) a novel compound of formula (I), including the compounds of formula (IA) or a salt thereof and (IB);

(b) a method for preparing a compound of formula (I), such as by esterification of a compound (IA) to prepare a compound of formula (IB);

(c) a pharmaceutical formulation comprising a non-toxic, effective amount of a compound of formula (IB) and a pharmaceutically acceptable carrier therefor;

(d) a method for preparing such formulations;

(e) a method for the prophylaxis or treatment of inflammation in a mammal, including man, comprising the administration to said mammal of a non-toxic, effective anti-inflammatory amount of a compound of formula (IB);

(f) a method for the prophylaxis or treatment of immunoregulatory conditions in a mammal, including man, comprising the administration to said mammal of a non-toxic, effective immunomodulatory amount of a compound of formula (IB);

(g) a compound of formula (IB) for use in medicine, such as in the inhibition of inflammation and/or the modulation of the immunoregulatory system;

(h) the use of a compound of formula (IB) in the preparation of a medicament, such as for the treatment or prophylaxis of inflammation and/or conditions associated with hyper or hypostimulation of the immune system; and (i) the use of a compound of formula (IA) in the preparation of a compound formula (IB).

The following examples are provided by way of illustration of the present invention. In the following Descriptions and Examples, the structures of the final products were determined by $^1$H and $^{13}$C NMR spectroscopy, using a JEOL JNM-GX 270 spectrometer. $^1$H and $^{13}$C chemical shifts were measured for solutions in CDCl$_3$ relative to the solvent. Ner refers to the tetracosenoyloxy chain, Lin to the γ-linolenoyloxy chain, Doc to the docosahexaenoyloxy chain and Pol to the propane-1,3-diol chain. All temperatures indicated are in degrees Celsius.

DESCRIPTION 1

Preparation of Starting Compound—z-15-Tetracosenoyl Chloride

Phosphorus pentachloride (0.123 mol, 25.6 g) was added gradually to a solution of nervonic acid (available from Aldrich Chemicals) (0.123 mol, 45.0 g) in dry ethyl ether (225 mL, C=200 g.L$^{-1}$). The mixture was stirred at room temperature under nitrogen for 3 h and concentrated to dryness to yield z-15-tetracosenoyl chloride as pale yellow, fairly viscous oil.

DESCRIPTION 2

Preparation of Comparative Compound—1,3-Di(z,z,z-6,9,12-Octadecatrienoyloxy)propane (GLA:GLA)

z,z,z-6,9,12-Octadecatrienoic acid (available from Sigma Chemicals) (0.180 mol, 50.0 g), propane-1,3-diol (0.086 mol, 6.5 g) and hypophosphorous acid (0.2 g) was heated with stirring to 160° C. under nitrogen. After 6 h, TLC (80:18:2 petroleum ether-ethyl ether-acetic acid) indicated that the reaction had gone to completion ($R_f$:0.56). The mixture was cooled down to room temperature and petroleum ether (700 mL) was added. The resulting solution was washed with saturated sodium bicarbonate (3×70 mL) and saturated sodium chloride (3×70 mL). It was then dried over anhydrous sodium sulphate and concentrated to dryness. Residual mono-ester and fatty acid were removed by distillation in vacuo (180° C., 10$^{-2}$ mbar). The resulting oil was dissolved in petroleum ether to make up a 33% solution and was passed down a silica column. Hexane was finally removed to yield 1,3-di-(z,z,z-6,9,12-octadecatrienoyloxy) propane as a colourless oil.

$^1$H NMR: δ: 0.89 (t, 6H, J=6.8 Hz, Lin-H$_{18}$), 1.31 (m, 12H, Lin-H$_{15-17}$), 1.41 (m, 4H, J=7.6 Hz, Lin-H$_4$), 1.65 (m, 4H, J=7.6Hz, Lin-H$_3$), 1.96 (m, 2H, J=6.4 Hz, Pol-H$_2$), 2.07 (dxt, 8H, J$_{4-5}$=J$_{14-15}$=5.4 Hz, J$_{5-6}$=J$_{13-14}$=6.8 Hz, Lin-H$_{5,14}$), 2.31 (t, 4H, J=7.3 Hz, Lin-H$_2$), 2.81 (t, 8H, J=5.6 Hz, Lin-H$_{8-11}$), 4.15 (t, 4H, J=6.8 Hz, Pol-H$_{1,3}$), 5.30–5.43 (m, 12H, Lin-H$_{6,7,9,10,12,13}$).

$^{13}$C NMR: δ: 14.0 (Lin-C$_{18}$), 22.5 (Lin-C$_{17}$), 24.5 (Lin-C$_3$), 25.6 (Lin-C$_{8,11}$), 26.8 (Lin-C$_5$), 27.2 (Lin-C$_{14}$), 28.0 (Pol-C$_2$), 29.0 (Lin-C$_4$), 29.3 (Lin-C$_{15}$), 31.5 (Lin-C$_{16}$), 34.1 (Lin-C$_2$), 60.8 (Pol-C$_{1,3}$) 127.5 (Lin-C$_{12}$), 128.0 (Lin-C$_9$), 128.2 (Lin-C$_7$), 128.3 (Lin-C$_{10}$), 129.5 (Lin-C$_6$), 130.4 (Lin-C$_{13}$), 173.5 (Lin-C$_1$).

DESCRIPTION 3

Preparation of 1-Hydroxy-3-(z-15-tetracosenoyloxy)propane

A solution of z-15-tetracosenoyl chloride, prepared according to Description 1, (0.129 mol, 49.7 g) in methylene chloride (500 mL) was added dropwise (over a period of 2.5–3 h) to a mixture of propane-1,3-diol (0.780 mol, 58.9 g) and triethylamine (0.323 mol, 32.6 g) in methylene chloride (1200 mL) at 0° C. under nitrogen. The mixture was left stirring in the ice bath for another 2 h, until TLC (80:18:2 petroleum ether-ethyl ether-acetic acid) showed that the by-product of the reaction started to form ($R_f$ product: 0.16; by-product: 0.63). The solution was washed with 2M sulphuric acid (2×150 mL), saturated sodium bicarbonate (3×300 mL) and saturated sodium chloride (2×300 mL). It was finally dried over anhydrous sodium sulphate, concentrated and purified by flash chromatography on silica gel (7:3 petroleum ether-ethyl ether) to yield 1-hydroxy-3-(z-15-tetracosenoyloxy)propane as a white solid.

$^1$H NMR: δ: 0.85 (t, 3H, J=6.7 Hz, Ner-H$_{24}$), 1.23 (m, 32H, Ner-H$_{4-13}$, Ner-His$_{18-23}$), 1.59 (m, 2H, J=7.3 Hz, Ner-H$_3$), 1.84 (m, 2H, J=6.1 Hz, Pol-H$_2$), 1.98 (dxt, 4H, J$_{14-15}$=J$_{16-17}$=5.3 Hz, J13$_{-14}$=J$_{17-18}$=6.4 Hz, Ner-H$_{14,17}$), 2.28 (t, 2H, J$_{2-3}$=7.3 Hz, Ner-H$_2$), 3.66 (t, 2H, J=6.1 Hz, Pol-H$_1$), 4.21 (t, 2H, J=6.1 Hz, Pol-H$_3$), 5.33 (m, 2H, J$_{14-15}$=J$_{16-17}$=5.3 Hz, Ner-H$_{15,16}$).

$^{13}$C NMR: δ: 14.1 (Ner-C$_{24}$), 22.7 (Ner-C$_{23}$), 25.0 (Ner-C$_3$), 27.2–29.8 (Ner-C$_{4-14}$, Ner-C$_{17-21}$), 31.8 (Pol-C$_2$), 31.9 (Ner-C$_{22}$), 34.3 (Ner-C$_2$), 59.2 (Pol-C$_1$), 61.1 (Pol-C$_3$), 129.9 (Ner-C$_{15,16}$), 174.3 (Ner-C$_1$).

DESCRIPTION 4

Preparation of Comparative Compound—Glyceryl Trinervonate

Nervonic acid was converted, using sodium ethanoate in ethanol, to the corresponding ethyl ester and the latter was reacted with glycerol at 160° C. This took place in solvent-free conditions using sodium ethoxide as catalyst. Water being removed at its formation, the equilibrium was easily shifted toward the formation of the triglyceride.

The following table shows the evolution of the reaction followed by GPC; after 10 h, 90% of the starting material was converted to glyceryl trinervonate.

TABLE D4

Preparation of glyceryl trinervonate from ethyl nervonate and glycerol

| Time | Triglycerides | Diglycerides | Monoglycerides | Ethyl Nervonate |
|---|---|---|---|---|
| 3 h | 56% | 26% | 3% | 15% |
| 5 h | 63% | 23% | 1% | 13% |
| 10 h | 90% | 0% | 0% | 10% |

Finally, the resulting mixture was distilled under vacuum, using a CD6 thin film laboratory scale evaporator at 220° C., 10$^{-3}$ mbar. Residual ethyl nervonate was successfully removed to leave pure glyceryl trinervonate as a white solid.

EXAMPLE 1

Preparation of 1-z,z,z-6,9,12-Octadecatrienoyloxy)-3-(z-15-tetracosenoyloxy)propane (NA:GLA)

A mixture of 1-hydroxy-3-(z-15-tetracosenoyloxy) propane, prepared according to Description 3, (0.045 mol, 19.0 g), z,z,z-6,9,12-octadecatrienoic acid (0.054 mol, 15.0 g) and hypophosphorous acid (0.4 g) was heated with stirring to 160° C. under nitrogen. After 5 h, TLC (80:18:2 petroleum ether-ethyl ether-acetic acid) indicated that most of the mono-ester had reacted ($R_f$: 0.60). The mixture was cooled down to room temperature and petroleum ether (800 mL) was added. The resulting solution was washed with saturated sodium bicarbonate (3×80 mL) and saturated sodium chloride (3×80 mL). It was then dried over anhydrous sodium sulphate, concentrated and purified by flash chromatography on silica gel (19:1 petroleum ether-ethyl ether) to yield 1-(z,z,z-6,9,12-octadecatrienoyloxy)-3-(z-15-tetracosenoyloxy)propane as a pale yellow oil.

$^1$H NMR: δ: 0.88 (t, 3H, J=6.8 Hz, Ner-H$_{24}$), 0.89 (t, 3H, J=6.8 Hz, Lin-H$_{18}$), 1.26–1.36 (m, 38H, Lin-H$_{15-17}$, Ner-H$_{4-13}$, Ner-H$_{18-23}$), 1.40 (m, 2H, J=7.8 Hz, Lin-H$_4$), 1.63 (m, 4H, Lin-H$_3$, Ner-H$_3$), 1.96 (m, 2H, J=6.3 Hz, Pol-H$_2$), 2.02 (m, 4H, Ner-H$_{14,17}$), 2.06 (m, 4H, Lin-H$_{5,14}$), 2.30 (m, 4H, J=7.6 Hz, Lin-H$_2$, Ner-H$_2$), 2.81 (t, 4H, J=5.8 Hz, Lin-H$_{8,11}$), 4.15 (t, 2H, J=6.3 Hz, Pol-H$_1$), 4.15 (t, 2H, J=6.3 Hz, Pol-H$_3$), 5.30–5.43 (m, 8H, Lin-H$_{6,17,9,10,12,13}$, Ner-H$_{15,16}$).

$^{13}$C NMR: δ: 14.0 (Lin-C$_{18}$), 14.1 (Ner-C$_{24}$), 22.6 (Lin-C$_{17}$), 22.7 (Ner-C$_{23}$), 24.5 (Lin-C$_3$), 24.9 (Ner-C$_3$), 25.6 (Lin-C$_{8,11}$), 26.8 (Lin-C$_5$), 28.0 (Pol-C$_2$), 29.1–29.8 (Lin-C$_{4,14,15}$, Ner-C$_{4-14}$, Ner-C$_{17-21}$), 31.5 (Lin-C$_{16}$), 31.9 (Ner-C$_{22}$), 34.1 (Lin-C$_2$), 34.2 (Ner-C$_2$), 60.8 (Pol-C$_{1,3}$), 127.6 (Lin-C$_{12}$), 128.0 (Lin-C$_9$), 128.3 (Lin-C$_7$), 128.4 (Lin-C$_{10}$), 129.5 (Lin-C$_6$), 129.9 (Ner-C$_{15,16}$), 130.4 (Lin-C$_{13}$), 173.5 (Lin-C$_1$), 173.7 (Ner-C$_1$).

EXAMPLE 2

Preparation of 1-(z-4,7,10,13,16,19-Docosahexaenoyloxy)-3-(z-15-tetracosenoyloxy) propane (NA:DHA)

(a) A mixture of 1-hydroxy-3-(z-15-tetracosenoyloxy) propane, prepared according to Description 3, (0.033 mol, 14.0 g), z-4,7,10,13,16,19-docosahexaenoic acid (0.040, 13.0 g) and hypophosphorous acid (0.3 g) was heated with stirring to 160° C. under nitrogen. After 5 h, TLC (80:18:2 petroleum ether-ethyl ether-acetic acid) indicated that most of the mono-ester had reacted (R$_f$: 0.56). The mixture was cooled down to room temperature and petroleum ether (600 mL) was added. The resulting solution was washed with saturated sodium bicarbonate (3×60 mL) and saturated sodium chloride (3×60 mL). It was then dried over anhydrous sodium sulphate, concentrated and purified by flash chromatography on silica gel (32:1 petroleum ether-ethyl ether) to yield 1-(z-4,7,10,13,16,19-docosahexaenoyloxy)-3-(z-15-tetracosenoyloxy)-3-propane as a pale yellow oil.

$^1$H NMR: δ: 0.88 (t, 3H, J=6.6 Hz, Ner-H$_{24}$), 0.97 (t, 3H, J=7.6 Hz, Doc-H$_{22}$), 1.26 (m, 32H, Ner-H$_{4-13}$, Ner-H$_{18-23}$), 1.61 (m, 2H, J=7.3 Hz, Ner-H$_3$), 1.96 (m, 2H, J=6.4 Hz, Pol-H$_2$), 2.03 (m, 4H, J=6.8 Hz, Ner-H$_{14,17}$), 2.08 (m, 2H, J=7.6 Hz, Doc-H$_{21}$), 2.29 (t, 2H, J=7.6 Hz, Ner-H$_2$), 2.37 (m, 4H, Doc-H$_{2,13}$), 2.85 (m, 10H, Doc-H$_{6,9,12,15,18}$), 4.15 (dxt, 4H, J$_{1,2}$=J$_{2,3}$=6.1 Hz, Pol-H$_{1,3}$), 5.33–5.40 (m, 14H, Doc-H$_{4,5,7,8,10,11}$, Doc-H$_{13,14,16,17,19,20}$, Ner-H$_{15,16}$).

$^{13}$C NMR: δ: 14.1 (Ner-C$_{24}$), 14.2 (Doc-C$_{22}$), 20.5 (Doc-C$_{21}$), 22.7 (Doc-C$_3$, Ner-C$_{23}$), 24.9 (Ner-C$_3$), 25.6 (Doc-C$_{6,9,12,15,18}$), 27.2–29.7 (Pol$_{C2}$, Ner-C$_{4-14}$, Ner-C$_{17-21}$), 31.9 (Ner-C$_{22}$), 34.1 (Doc-C$_2$), 34.2 (Ner-C$_2$), 60.7 (Pol-C$_3$), 61.0 (Pol-C$_1$), 127.0 (Doc-C$_{19}$), 127.8 (Doc-C$_{5,16}$), 128.0–128.2 (Doc-C$_{7,8,10,11,13,14}$), 128.5 (Doc-C$_{17}$), 129.3 (Doc-C$_4$), 129.9 (Ner-C$_{15,16}$), 132.0 (Doc-C$_{20}$), 172.9 (Doc-C$_1$), 173.7 (Ner-C$_1$).

EXAMPLE 3

Preparation of 1,3-di-(z-15-Tetracosenoyloxy) propane (NA:NA)

z-15-Tetracosenoic acid (available from Sigma Chemicals), (0.286 mol, 104.7 g), propane-1,3-diol (0.136, 10.3 g) and hypophosphorous acid (0.4 g) was heated with stirring to 160° C. under nitrogen. After 6 h, TLC (80:18:2 petroleum ether-ethyl ether-acetic acid) indicated that the reaction had gone to completion (R$_f$: 0.63). The mixture was cooled down to room temperature and petroleum ether (1500 mL) was added. The resulting solution was washed with saturated sodium bicarbonate (3×150 mL) and saturated sodium chloride (3×150 mL). It was then dried over anhydrous sodium sulphate and concentrated to dryness. Residual mono-ester and fatty acid were removed by distillation in vacuo (230° C., 10$^{-2}$ mbar). The resulting oil was dissolved into petroleum ether to make up a 33% solution and was passed down a silica column. Hexane was finally removed to yield 1,3-di-(z-15-tetracosenoyloxy)propane as a colourless oil.

$^1$H NMR: δ: 0.88 (t, 6H, J=6.8 Hz, Ner-H$_{24}$), 1.26 (m, 64H, Ner-H$_{4-13}$, Ner-H$_{18-23}$), 1.59 (m, 4H, J=7.6Hz, Ner-H$_3$), 1.96 (m, 2H, J=6.3 Hz, Pol-H$_2$), 2.01 (dxt, 8H, J$_{14-15}$=J$_{16-17}$=5.6 Hz, J13$_{-14}$=J$_{17-18}$=6.5 Hz, Ner-H$_{14,17}$), 2.29 (m, 4H, J$_{2-3}$=7.6 Hz, Ner-H$_2$), 4.15 (t, 4H, J=6.3 Hz, Pol-H$_{1,3}$), 5.34 (m, 4H, J$_{14-15}$=J$_{16-17}$=5.6 Hz, Ner-H$_{15,16}$).

$^{13}$C NMR: δ: 14.1 (Ner-C$_{24}$), 22.7 (Ner-C$_{23}$), 24.9 (Ner-C$_3$), 27.2–29.8 (Ner-C$_{4-14}$, Ner-C$_{17-21}$, Pol-C$_2$), 31.9 (Ner-C$_{22}$), 34.2 (Ner-C$_2$), 60.8 (Pol-C$_{1,3}$), 129.9 (Ner-C$_{15,16}$), 173.7 (Ner-C$_1$).

EXAMPLE 4

Comparison Between NA:NA and GLA:GLA in EAE

The prophylactic effect of GLA:GLA (Description 2) and NA:NA (Example 3) on the emergence and development of neurological experimental allergic encephalomyelitis (EAE) in the Lewis rat was compared, as follows:

Materials and Methods (a) Induction of EAE

Male Lewis rats, weighing 230–290 g on the day of inoculation, were injected in each rear footpad with 0.1 ml of an emulsion containing equal parts of guinea pig spinal cord; phosphate buffered saline (PBS) and incomplete Freund's adjuvant supplemented with 10 mg/ml *Mycobacterium tuberculosis* H$_{37}$Ra.

(b) Assessment of EAE

Animals were weighed daily and assessed for neurological disease from day 7 post-inoculation (PI). Rats displaying symptoms of EAE were scored as follows: 1: flaccid tail (FT), 2: hind limb hypotonia (HLH), 3: partial hind limb paralysis (PHLP), 4: complete hind limb paralysis (CHLP), 5: moribund or dead.

(c) Dosing Regime

GLA:GLA and NA:NA (neat oils) were orally administered (at 45° C.) 5 days prior to inoculation and for 25 days post-inoculation at a dose of 1000 mg/kg body weight/day. Control-sensitised animals received PBS vehicle or were undosed and each treatment contained 7 animals. Individual brains and blood samples were then collected and stored at −20° C. prior to fatty acid analysis. NA:NA treatment for 2 animals was terminated on day 21, as the rats resisted repeated attempts to administer the drug orally.

Results (a) Mean Body Weight Changes

Undosed sensitised rats and animals receiving vehicle lost body weight between 10 and 12 days PI. Rats treated with GLA:GLA and NA:NA showed weight loss beginning 10 days PI. Animals in all treatments increased body weight 18–20 days PI.

(b) Onset and Loss of Symptoms

Undosed rats and vehicle-treated animals showed initial signs of disease between 11 and 12 days PI (Table 1). Symptom onset, loss of signs and disease duration in GLA:GLA and NA:NA rats was not significantly different compared to control groups. Interestingly, all animals treated with NA:NA survived compared to control and GLA:GLA treated groups.

TABLE 1

GLA:GLA and NA:NA and the occurrence and development of EAE

| Treatment | Number diseased/ total | Mean day of symptom onset (±SD) | Mean day of final symptom loss (±SD) | Mean duration of symptoms (day ± SD) | Number of dead/ total |
| --- | --- | --- | --- | --- | --- |
| Undosed | 7/7 | 12.4 ± 1.0 | 17.8 ± 1.2 | 5.4 ± 1.1 | 1/7 |
| Vehicle | 7/7 | 11.6 ± 0.8 | 18.4 ± 1.1 | 6.8 ± 1.1 | 2/7 |
| GLA:GLA | 7/7 | 11.9 ± 0.9 | 18.0 ± 0.7 | 6.1 ± 0.8 | 2/7 |
| NA:NA | 7/7 | 12.4 ± 1.5 | 17.6 ± 1.6 | 5.2 ± 1.6 | 0/7 |

(c) Incidence and Severity of EAE

The mean cumulative neurological scores, a graphical expression of daily disease development, for undosed and vehicle-treated rats were comparable during the early stages of EAE. The cumulative data recorded for animals receiving vehicle became in excess of values noted for undosed rats but similar to the disease profile displayed by the GLA:GLA-treated group. EAE-inoculated rats treated with NA:NA had scores consistently lower than undosed and vehicle treatments beginning 14 days PI.

All control, vehicle-treated and GLA:GLA-dosed rats showed FT and HLH (Table 2). Interestingly, only 4/7 animals treated with NA:NA displayed initial disease symptoms. Furthermore, no animals receiving NA:NA experienced PHLP or CHLP in marked contrast to control vehicle and GLA:GLA-treated groups. In addition, NA:NA-dosed animals appeared more alert and less incontinent compared to undosed and vehicle-treated rats.

TABLE 2

The effect of GLA:GLA and NA:NA on the severity of EAE

| Symptom | Treatment* | | | |
| --- | --- | --- | --- | --- |
| | Undosed | Vehicle | GLA:GLA | NA:NA |
| FT | 7/7 | 7/7 | 7/7 | 7/7 |
| HLH | 7/7 | 7/7 | 7/7 | 4/7 |
| PHLP | 3/7 | 5/7 | 4/7 | 0/7 # |
| CHLP | 1/7 | 3/7 | 3/7 | 0/7 |

*Number of animals showing symptoms/total
$P < 0.01$ NA:NA v Vehicle. Fischer's exact probability test Conclusions Treatment of EAE-inoculated rats with GLA:GLA did not alter the course of neurological EAE compared to undosed rats and those having vehicle treatments. However, dosing EAE-sensitised animals with NA:NA clearly reduced the overall intensity of disease and, in particular, significantly reduced the incidence of partial paralysis compared to the vehicle treatment. The results suggest NA:NA has an immunomodulatory or anti-inflammatory mode of action on the development of EAE.

Comparative Example: Glyceryl Trinervonate in EAE

Prophylactic effects of glyceryl trinervonate (GTN, Description 4) were assessed on acute EAE in the Lewis rat. Induction and Assessment of EAE was as for Example 4. Dosing regime involved oral administration in Miglyol 810 five days prior to inoculation and for 20 days post-inoculation. (Refer to Example 8 regarding insignificance of use of PBS or Miglyol vehicles).

Results (a) Body Weight Changes:

Animals gained weight until day 10, showing dietary administered GTN did not induce any major adverse effect. The results show the characteristic body weight loss in both control and treated animals preceding the onset of symptoms. Values for control and treated animals were not different.

(b) Neurological Scores—Incidence and Severity of EAE

All inoculated animals showed neurological deficits associated with EAE. The onset and loss of symptoms together with the duration of the disease in GTN-treated animals were not significantly different from vehicle or undosed groups (Table 3).

TABLE 3

Neurological symptoms in EAE-sensitised rats

| Treatment | No. of diseased rats | Mean day of symptom onset | Mean day of symptom loss | Mean duration of symptoms (days) | Number of dead |
| --- | --- | --- | --- | --- | --- |
| Undosed | 10/10 | 11.3 ± 1.3 | 17.1 ± 1.0 | 5.8 ± 1.3 | 0/10 |
| Vehicle | 10/10 | 11.5 ± 0.5 | 17.0 ± 0.5 | 5.5 ± 0.5 | 0/10 |
| GTN | 10/10 | 11.2 ± 1.2 | 17.0 ± 1.2 | 5.8 ± 1.1 | 0/10 |

Table 4 shows 70–80% of undosed and vehicle-treated rats experienced paralytic disease and data obtained from animals receiving GTN confirm the treatment did not significantly affect any parameter associated with neurological deficits in EAE-diseased rats.

TABLE 4

Severity of neurological symptoms in EAE-sensitised rats.

| Symptom or Status | Treatment | | |
| --- | --- | --- | --- |
| | Undosed (%)* | Vehicle (%)* | GTN (%)* |
| PFT | 100 | 100 | 100 |
| CFT | 100 | 100 | 100 |
| HLH | 90 | 100 | 90 |
| PHLP | 70 | 80 | 70 |
| CHLP | 30 | 60 | 40 |
| MD | 0 | 0 | 0 |

*Percentage of rats in the group; n = 10 animals for all groups.

Conclusions

These results established that NA does not cross the blood-brain barrier in this form. This is surprising, since GTN has an O-ester linkage, which binds nervonic acid molecules to glycerol. Glycerol is widely encountered in the structure of brain lipids, acting as a carrier able to cross the brain-blood barrier, and might have been expected to facilitate passage of lipids such as NA across this membrane. This test shows that prior ideas regarding suitable lipid carriers cannot be applied to NA.

EXAMPLE 5

NA:NA (Ethyl Oleate Formulation) in EAE

The prophylactic effect of the compound of Example 3 (NA:NA), using an alternative formulation, on the emergence and development of neurological EAE in the Lewis rat was assessed as follows:

Materials and Methods (a) Induction of EAE

Male Lewis rats, weighing 240–360 g on the day of inoculation, were injected in each rear footpad with 0.1 ml of an emulsion containing equal parts of guinea pig spinal cord, phosphate buffered saline (PBS) and incomplete Freund's adjuvant supplemented with 10 mg/ml *Mycobacterium tuberculosis* $H_{37}Ra$.

(b) Assessment of EAE

Animals were weighed daily and assessed for neurological disease from day 7 post-inoculation (PI). Rats displaying symptoms of EAE were scored as follows: 1: flaccid tail (FT), 2: hind limb hypotonia (HLH), 3: partial hind limb paralysis (PHLP), 4: complete hind limb paralysis (CHLP), 5: moribund or dead.

(c) Dosing Regime

NA:NA (10% w/w solution in ethyl oleate B.P.) was orally administered (at 35–37° C.) 5 days prior to inoculation and for 22 days PI at a dose of 1000 mg/kg body weight/day. Control-sensitised animals received ethyl oleate vehicle or were undosed, and each treatment contained 10 animals. On day 23 PI, individual rat brains and plasma samples were collected and stored at −20° C. prior to fatty acid analysis.

Statistical Analysis

Students t-test was used to assess significant differences in neurological scores and the Fishers exact probability test for the presence or absence of symptoms.

Results (a) Mean Body Weight Changes

Undosed sensitised rats and animals receiving either vehicle or NA:NA experienced characteristic body weight loss between 10 and 12 days PI. Animals in all treatments increased body weight 16–18 days PI.

(b) Onset and Loss of Symptoms

All undosed and vehicle-treated sensitised rats showed neurological signs of EAE (Table 3). In contrast, only 60% of animals receiving NA:NA experienced symptoms of disease. The mean day of symptom onset and loss was not significantly altered by NA:NA treatment. The mean duration of symptoms in rats receiving NA:NA was reduced, but not significantly, compared to undosed and ethyl oleate-treated groups.

TABLE 5

NA:NA in ethyl oleate on the occurrence and development of EAE

| Treatment | Number diseased/ total | Mean day of symptom onset (±SD) | Mean day of final symptom loss (±SD) | Mean duration of symptoms (day ± SD) | Number of dead/ total |
|---|---|---|---|---|---|
| Undosed | 10/10 | 11.7 ± 0.5 | 16.6 ± 0.5 | 4.9 ± 0.6 | 2/10 |
| Vehicle | 10/10 | 12.2 ± 0.6 | 17.2 ± 0.6 | 4.9 ± 0.9 | 0/10 |
| NA:NA | 6/10* | 12.3 ± 0.8 | 16.3 ± 1.0 | 4.0 ± 1.2 | 0/10 |

*NA:NA compared to undosed and vehicle groups $P < 0.05$ (c) Incidence and Severity of EAE Neurological scores for NA:NA dosed rats were consistently lower compared to values recorded for undosed and vehicle-treated animals. The mean cumulative neurological scores for undosed rats and animals receiving ethyl oleate were similar for the duration of the study. In contrast, cumulative scores for rats treated with NA:NA were reduced 12–13 days PI and were markedly lower than control values for the remainder of the study.

The number of NA:NA-dosed rats showing FT and HLH was significantly reduced compared to undosed and vehicle treatments (Table 6 FT: $P<0.05$, HLH: $P<0.01$). In addition, fewer animals receiving NA:NA experienced paralytic symptoms of EAE. Furthermore, NA:NA treated rats were more alert and aware of their surroundings and less incontinent compared to control groups.

TABLE 6

Effect of NA:NA in ethyl oleate on the severity of EAE

| | Treatment* | | |
|---|---|---|---|
| Symptom | Undosed | Vehicle | NA:NA |
| FT | 10/10 | 10/10 | 6/10** |
| HLH | 10/10 | 10/10 | 4/10*** |
| PHLP | 6/10 | 7/10 | 3/10 |
| CHLP | 2/10 | 2/10 | 1/10 |

*Number of animals showing symptoms/total
**NA:NA compared to undosed and vehicle groups $P < 0.05$
***NA:NA compared to undosed and vehicle groups $P < 0.01$ Conclusions This study clearly shows that NA:NA significantly reduces the incidents of disease and inhibits the occurrence of initial non-paralytic symptoms, despite prior characteristic body weight loss in all treated rats. Also, daily neurological scores were markedly reduced by NA:NA treatment.

The previous study (Example 4) to determine the efficacy of NA:NA in EAE showed that the compound reduced the overall intensity of the disease and significantly suppressed paralytic symptoms compared to vehicle treatment. The current investigation (Example 5) has shown that reformulation of NA:NA in ethyl oleate facilitated administration (allowing its temperature to be reduced to 35–37° C.) without the loss of compound efficacy in EAE.

The results clearly indicate NA:NA has an immunomodulatory or anti-inflammatory profile of activity in acute rat EAE.

EXAMPLE 6

NA:DHA and NA:GLA in EAE Tests

The prophylactic effect of the compounds of Example 1 (NA:GLA) and Example 2 (NA:DHA) on the emergence and development of neurological EAE in the Lewis rat was assessed as follows:

Materials and Methods (a) Induction of EAE

Male Lewis rats, weighing 230–280 g on the day of inoculation, were injected in each rear footpad with 0.1 ml of an emulsion containing equal parts of guinea pig spinal cord; phosphate buffered saline (PBS) and incomplete Freund's adjuvant supplemented with 10 mg/ml *Mycobacterium tuberculosis* $H_{37}Ra$.

(b) Assessment of EAE

Animals were weighed daily and assessed for neurological disease from day 7 post-inoculation (PI). Rats displaying symptoms of EAE were scored as follows: 1: flaccid tail (FT), 2: hind limb hypotonia (HLH), 3: partial hind limb paralysis (PHLP), 4: complete hind limb paralysis (CHLP), 5: moribund or dead.

(c) Dosing Regime

NA:GLA (neat oil) was orally administered 5 days prior to inoculation and continued for 25 days PI, at a dose of 750 mg/kg body weight/day and 1000 mg/kg body weight/day. NA:DHA (neat oil) was given by an identical dosing regime at a dose of 500 mg/kg body weight/day. Control-sensitised animals received PBS vehicle or were undosed. Undosed, vehicle and low dose NA:GLA treatments contained 7 animals. Four rats received high dose NA:GLA and 3 rats were dosed with NA:DHA. Individual brains and blood samples were then collected for analysis.

Results (a) Mean Body Weight Changes

Undosed, sensitised rats and animals receiving vehicle lost weight between 8 and 10 days. Similarly, rats treated with NA:DHA showed body weight loss beginning 8 days after inoculation. However, NA:DHA-treated rats had a greater increase in body weight during the week following sensitisation compared to control and dosed groups. Body weight loss experienced by animals treated with low and high dose NA:GLA began 2 days later than recorded in other treatments.

(b) Onset and Loss of Symptoms

Undosed rats and animals receiving vehicle showed initial signs of disease between 10 and 11 days PI (Table 7).

TABLE 7

NA:GLA and NA:DHA, and the occurrence and development of EAE

| Treatment (mg/kg/day) | Number diseased/total | Mean day of symptom onset (±SD) | Mean day of final symptom loss (±SD) | Number of dead/total |
|---|---|---|---|---|
| Undosed | 7/7 | 10.7 ± 0.8 | 20.3 ± 0.8 | 0/7 |
| Vehicle | 7/7 | 10.9 ± 1.2 | 19.2 ± 1.3 | 2/7 |
| NA:GLA (750) | 7/7 | 11.3 ± 0.8 | 19.0 ± 0.8 | 0/7 |
| NA:GLA (1000) | 4/4 | 11.3 ± 0.5 | 18.8 ± 1.3 | 0/4 |
| NA:DHA (500) | 3/3 | 10.3 ± 0.6 | 19.3 ± 1.2 | 0/3 |

Onset of disease in NA:GLA-treated rats was delayed and accelerated in animals administered NA:DHA compared to control groups. However, the values for dosed animals were not significantly different from data recorded for undosed and vehicle treatments.

(c) Incidence and Severity of EAE

The mean cumulative clinical scores, a graphical expression of daily disease development, for undosed and vehicle-treated rats was comparable throughout the experiment. Data recorded for animals receiving low and high dose NA:GLA were consistently lower than control values for the duration of the study. The daily score for rats treated with NA:DHA was enhanced compared to levels noted for control and NA:GLA-treated animals. All control and drug-treated rats showed FT and HLH (Table 8). However, fewer animals receiving NA:GLA experienced PHLP (low dose: 57%/high dose: 50%) and CHLP (low dose: 43%/high dose: 25%) compared to controls and NA:DHA-treated rats. Also, the development of CHLP in rats receiving NA:DHA was earlier (11.3±1.3 and 12.7±1.3 respectively).

TABLE 8

The effects of NA:GLA and NA:DHA on the severity of EAE

| | Treatment* (mg/kg/day) | | | | |
|---|---|---|---|---|---|
| Symptom | Undosed | Vehicle | NA:GLA (750) | NA:GLA (1000) | NA:DHA (500) |
| FT | 7/7 | 7/7 | 7/7 | 4/4 | 3/3 |
| HLH | 7/7 | 7/7 | 7/7 | 4/4 | 3/3 |

TABLE 8-continued

The effects of NA:GLA and NA:DHA on the severity of EAE

| | Treatment* (mg/kg/day) | | | | |
|---|---|---|---|---|---|
| Symptom | Undosed | Vehicle | NA:GLA (750) | NA:GLA (1000) | NA:DHA (500) |
| PHLP | 7/7 | 7/7 | 4/7 | 2/4 | 3/3 |
| CHLP | 6/7 | 7/7 | 3/7 | 1/4 | 3/3 |

*Number of animals showing symptoms/total

Conclusions

Prophylactic administration of NA:GLA, at 750 and 1000 mg/Kg body weight/day, to acute EAE-sensitised rats delayed the onset and clearly reduced the incidence and severity of disease compared to control groups. The results suggest the compound has immunosuppressive or anti-inflammatory activity, which influenced the immunological response to neuro-antigen and the subsequent manifestation of disease. In contrast, treatment with NA:DHA intensified neurological symptoms, possibly through an enhancement of the induction phase of EAE, suggesting the compound may act as an immunopotentiator.

EXAMPLE 7

Evaluation of NA:NA and NA:GLA in Mice

The prophylactic effect of the compounds of Example 3 (NA:NA) and Example 1 (NA:GLA) were assessed on chronic EAE in the Biozzi mouse model.

Materials and Methods (a) Induction of EAE

Male Biozzi mice weighing 30–35 g were injected in each flank with 0.15 mL of an emulsion containing lyophilised mouse spinal cord, phosphate buffered saline and incomplete Freund's adjuvant supplemented with *Mycobacterium butyricum* and *Mycobacterium tuberculosis* $H_{37}Ra$.

(b) Assessment of EAE

Animals were weighed daily and assessed for neurological disease from day 7 post-inoculation (PI). Mice displaying symptoms of EAE were scored as follows:

1: Partial Flaccid Tail (PFT), 2: Complete Flaccid Tail (CFT), 3: Impaired Righting Reflex (IRR), 4: Ataxic Gait (AG), 5: Hind Limb Hypotonia (HLH), 6: Partial Hind Limb Paralysis (PHLP), 7: Complete Hind Limb Paralysis (CHLP), 8: Moribund (M), 9: Dead (D).

(c) Dosing Regime

NA:NA and NA:GLA (both 10% w/w solution in ethyl oleate B.P.) were orally administered (at 35–37° C.) 5 days prior to inoculation and for 43 days PI at a dose of 1000 mg/kg body weight/day. Control sensitised animals received ethyl oleate vehicle or were undosed, and each treatment contained 10 animals. Individual brain and blood samples were then collected for analysis at 4344 days PI.

Results (a) Mean Body Weight Changes:

The mean body weights of chronic EAE-sensitised mice receiving vehicle, NA:GLA or NA:NA decreased between −4 and 2 days post-inoculation.

A dramatic reduction in body weight occurred in undosed mice 16 days post-inoculation, whilst no similar weight loss was recorded in animals receiving vehicle, NA:GLA or NA:NA. The mean body weights of undosed mice and animals receiving vehicle and NA:NA steadily increased and became comparable 13–40 days post-inoculation. However, mice treated with NA:GLA did not experience similar increase in body weight. All groups showed body weight loss 40–44 days post inoculation.

(b) Neurological Scores—Incidence and Severity of Chronic Relapsing EAE:

The onset of acute symptoms appeared in 80% of undosed mice approximately 20 days PI (Table 9). In contrast, only 20–30% of animal showed acute disease in vehicle and compound-treated groups. Mice receiving NA-NA lost signs of acute disease earlier and consequently the duration of deficits was shorter compared to diseased mice in other groups.

TABLE 9

Incidence and development of acute phase in chronic relapsing EAE-sensitised mice

| Treatment | No. of diseased Mice | Mean day of symptom onset | Mean day of symptom loss | Mean duration of symptoms (days) | Number of dead mice |
|---|---|---|---|---|---|
| Undosed | 8/10 | 19.9 ± 4.2 | 31.9 ± 1.6 | 12.0 ± 4.2 | 0/10 |
| Vehicle | 2/10 | 21.0 ± 5.7 | 29.0 ± 2.4 | 8.0 ± 4.2 | 0/10 |
| NA-GLA | 3/10 | 21.7 ± 4.2 | 30.0 ± 1.4 | 5.7 ± 1.5 | 0/10 |
| NA-NA | 3/10 | 22.3 ± 3.8 | 24.7 ± 3.2 | 2.3 ± 1.2 | 0/10 |

Fewer compound-treated mice suffered a relapse compared to undosed animals (Table 10). However, a similar number of mice receiving vehicle experienced a recurrence of symptoms. Interestingly, the onset of relapse was delayed, but not significantly, in animals dosed with NA:GLA and NA:NA.

TABLE 10

Incidence and development of relapse phase in chronic relapsing EAE-sensitised mice

| Treatment | No. of diseased mice | Mean day of symptom onset | Mean day of symptom loss | Mean duration of symptoms (days) | Number of dead mice |
|---|---|---|---|---|---|
| Undosed | 9/10 | 35.6 ± 2.7 | * | * | 0/10 |
| Vehicle | 2/10 | 40.0 ± 0.0 | * | * | 0/10 |
| NA-GLA | 3/10 | 42.0 ± 1.0 | * | * | 0/10 |
| NA-NA | 3/10 | 43.3 ± 1.2 | * | * | 1/10 |

*The evaluation was terminated before the relapse phase ended

Tables 11 and 12 describe the percentage of undosed vehicle and compound-treated mice showing the progressive symptoms of acute and relapsing disease. The results clearly demonstrate that acute and relapsing symptoms in vehicle-treated animals are suppressed compared to the occurrence of disease in undosed mice. Furthermore, the neurological signs shown by vehicle-treated mice are similar to symptoms experienced by animals receiving NA:GLA and NA:NA. The mean neurological scores for undosed chronic relapsing EAE-sensitised mice characteristically increased 2 to 3 weeks after the initial inoculation.

A remission of symptoms occurred 25–33 days post sensitisaton followed by a relapse of neurological deficits. Acute and relapse symptoms were markedly reduced in animals receiving vehicle, NA:GLA and NA:NA. In particular, neurological symptoms during the acute and relapse phases of chronic relapsing EAE were completely abolished in mice treated with NA:NA.

TABLE 11

The severity of acute phase in chronic relapsing EAE-sensitised mice

| Symptom or Status | Treatment | | | |
|---|---|---|---|---|
| | Undosed (%)* | Vehicle (%)* | NA-GLA (%)* | NA-NA (%)* |
| PFT | 80 | 20 | 20 | 10 |
| CFT | 80 | 10 | 20 | 0 |
| AG | 60 | 10 | 20 | 20 |
| HLH | 80 | 20 | 30 | 10 |
| PHLP | 50 | 10 | 20 | 0 |
| CHLP | 30 | 0 | 20 | 0 |

*Percentage of mice in the group; n = 10 animals for all groups

TABLE 12

Severity of relapse phase in chronic relapsing EAE-sensitised mice

The severity of acute phase in chronic relapsing EAE-sensitised mice

| Symptom or Status | Treatment | | | |
|---|---|---|---|---|
| | Undosed (%)* | Vehicle (%)* | NA-GLA (%)* | NA-NA (%)* |
| PFT | 40 | 0 | 10 | 20 |
| CFT | 20 | 0 | 10 | 0 |
| AG | 40 | 0 | 10 | 30 |
| HLH | 60 | 10 | 30 | 30 |
| PHLP | 50 | 0 | 0 | 0 |
| CHLP | 0 | 0 | 0 | 0 |

*Percentage of mice in the group; n = 10 animals for all groups

Conclusions

The results show that treatment of chronic relapsing EAE-inoculated mice with the vehicle, ethyl oleate, significantly reduced the incidence and severity of the acute and relapsing phases of chronic relapsing EAE in this test.

The modification of chronic relapsing EAE by vehicle treatment—the vehicle acts as a solvent for the drug and facilitates its administration—prevents a clear assessment of compound efficacy in chronic EAE and is in contrast to initial studies in the rat where ethyl oleate was also employed (see Example 5).

Nevertheless, the results suggest that NA:GLA and NA:NA treatment, particularly in combination with ethyl oleate, has the potential to limit the duration of acute disease and to delay the onset of relapse symptoms. This supports the conclusions of the above Examples of compound efficacy in acute rat EAE.

EXAMPLE 8

The Use of Miglyol as a Vehicle in the Treatment of Chronic Relapsing EAE in the Mouse Model The use of a vehicle without the ability to modify the course of chronic relapsing EAE in the Biozzi mouse was therefore studied. This experiment only involved PBS, Miglyol and ethyl oleate, which are drug-vehicles and were evaluated in order to assess their neutrality on the course of EAE.

Miglyol 810, which is a mixture of triglycerides bearing 8–10 carbon atom acyl chains, first underwent a comparative study with PBS (phosphate-buffered saline, aqueous solution) to ascertain its neutrality vis-à-vis EAE conditions.

PBS is a reference vehicle and is known not to alter the course of EAE. Prophylactic effects of Miglyol 810 were assessed on chronic relapsing EAE (CREAE) in the Biozzi mouse model according to a method similar to that of Example 7, but using Miglyol 810 vehicle and post-inoculation treatment to day 30 at a dose of 10 g/kg bodyweight/day. [Explanation of dose regime: When a study involves a test compound such as NA:NA, the dose indicated only refers to the amount of test compound administrated, not to the amount of vehicle+compound. In this vehicle study, since no test compound such as NA:NA was present, the dose refers to the amount of vehicle, ie 10 times higher than the amount of test compound that would have been present, in accord with all other studies in the mouse model.]

The results clearly demonstrated that all mice inoculated for CREAE showed established acute paralytic symptoms. In particular, the course of the disease was not influenced by repeated oral dosing with either PBS or Miglyol.

Therefore, Miglyol appeared well-suited for use as a vehicle in subsequent studies to determine the efficacy of compounds in CREAE. Therefore, using Miglyol 810 as the new vehicle, prophylactic effects of NA:NA and NA:GLA were re-assessed on CREAE in the Biozzi mouse model (90% dilution, 1000 mg/kg/day, up to 43 days PI).

Results (a) Body Weight Changes

The mean body weights of CREAE-sensitised mice receiving vehicle and NA:GLA decreased between 1 and 4 days PI, contrary to undosed and NA:NA treated mice.

The onset and progression of symptoms caused a dramatic reduction in body weight, which occurred in all groups of animals between 12 and 22 days PI, however body weight losses for drug treated animals were less important than for undosed and vehicle groups.

Body weight gain was experienced by animals in all groups between 23 and 31 days PI, which corresponded with the loss of neurological deficits. Interestingly, contrary to undosed and vehicle treated animals, body weight still continued to rise for NA:GLA and NA:NA treated mice during the onset and progression of symptoms of the relapsing phase from 32 days PI.

(b) Neurological Scores—Incidence and Severity of CREAE

Animals in each treatment were highly affected by the acute stage of CREAE. Mice receiving NA:GLA had a shorter duration of symptoms compared to NA:NA, undosed and vehicle treated animals (Table 13).

Almost all animals in each group suffered a relapse (Table 14). There was no difference in the onset of symptoms between groups; however, the duration of symptoms was significantly reduced for NA:GLA treated mice compared to NA:NA, undosed and vehicle groups.

Surprisingly, NA:NA treated animals showed a longer duration of symptoms.

TABLE 13

Incidence and development of acute phase in CREAE-sensitised mice

| Treatment | No. of diseased Mice | Mean day of symptom onset | Mean day of symptom loss | Mean duration of symptoms (days) | Number of dead mice |
|---|---|---|---|---|---|
| Undosed | 12/12 | 15.8 ± 1.5 | 26.7 ± 1.0 | 10.9 ± 1.2 | 2/12 |
| Vehicle | 12/12 | 16.8 ± 2.2 | 26.3 ± 2.4 | 9.0 ± 2.9 | 3/12 |
| NA:GLA | 10/11 | 17.9 ± 2.6 | 25.9 ± 2.0 | 6.9 ± 3.0 | 1/11 |
| NA:NA | 12/12 | 17.1 ± 1.9 | 26.3 ± 1.0 | 9.2 ± 1.6 | 1/12 |

TABLE 14

Incidence and development of relapse phase in CREAE-sensitised mice

| Treatment | No. of diseased mice | Mean day of symptom onset | Mean day of symptom loss | Mean duration of symptoms (days) | Number of dead mice |
|---|---|---|---|---|---|
| Undosed | 9/10 | 32.1 ± 3.6 | 43.7 ± 3.5 | 10.8 ± 3.6 | 0/10 |
| Vehicle | 8/9 | 33.5 ± 1.7 | * | * | 5/9 |
| NA:GLA | 8/9 | 33.1 ± 4.9 | 39.8 ± 5.0 | 7.0 ± 4.2 | 3/9 |
| NA:NA | 9/11 | 34.3 ± 6.6 | 44.0 ± 3.6 | 13.7 ± 4.0 | 3/11 |

*One animal lost paralytic symptoms 45 days Pl. Remaining mice either died or showed paralysis.

Tables 15 and 16 describe the percentage of undosed, vehicle, and compound-treated mice showing the progressive symptoms of acute and relapsing disease. The results clearly show that acute and relapsing symptoms in NA:GLA treated animals are diminished compared to the occurrence of disease in other groups of mice. Furthermore, the symptoms shown by NA:NA treated mice appear to be similar to symptoms experienced by animals receiving the vehicle or no treatment.

The mean neurological scores for undosed and vehicle-treated mice characteristically increased 2 weeks after the initial inoculation. Scores obtained with NA:NA treatment were not different from both control groups in the acute phase of the disease and only slightly lower in the relapsing phase. In contrast to these results, animals treated with NA:GLA had lower scores in both acute and relapsing phases.

TABLE 15

The severity of acute phase in CREAE-sensitised mice

| Symptom or Status | Treatment | | | |
|---|---|---|---|---|
| | Undosed (%)* | Vehicle (%)* | NA-GLA (%)* | NA-NA (%)* |
| PFT | 100 | 100 | 91 | 100 |
| CFT | 100 | 100 | 82 | 100 |
| IRR | 100 | 100 | 82 | 100 |
| AG | 100 | 100 | 73 | 100 |
| HLH | 100 | 100 | 73 | 100 |
| PHLP | 92 | 75 | 46 | 75 |
| CHLP | 92 | 58 | 36 | 58 |
| M | 0 | 0 | 0 | 0 |
| D | 17 | 25 | 9 | 8 |

*Percentage of mice in the group; n = 12 animals for all groups, except for NA:GLA where n = 11

TABLE 16

The severity of relapse phase in CREAE-sensitised mice

| Symptom or Status | Treatment | | | |
|---|---|---|---|---|
| | Undosed (%)* | Vehicle (%)* | NA:GLA (%)* | NA:NA (%)* |
| PFT | 90 | 89 | 89 | 82 |
| CFT | 80 | 89 | 67 | 82 |
| IRR | 80 | 89 | 67 | 82 |
| AG | 70 | 89 | 56 | 82 |
| HLH | 70 | 78 | 56 | 82 |
| PHLP | 70 | 78 | 56 | 73 |

TABLE 16-continued

The severity of relapse phase in CREAE-sensitised mice

| Symptom or Status | Treatment | | | |
|---|---|---|---|---|
| | Undosed (%)* | Vehicle (%)* | NA:GLA (%)* | NA:NA (%)* |
| CHLP | 60 | 67 | 44 | 73 |
| M | 0 | 0 | 11 | 0 |
| D | 0 | 56 | 22 | 27 |

*Percentage of mice in the group: n = 9 animals for vehicle and NA:GLA groups, n = 10 for undosed group and n = 11 for NA:NA group Conclusions The results obtained for undosed and vehicle treated groups were not different and confirmed that Miglyol 810 did not alter the course of the disease.

However, the effects of NA:NA and NA:GLA on the neurological course of chronic-relapsing EAE (CREAE) were different from the initial evaluation.

Surprisingly, NA:NA did not seem significantly to alter the course of CREAE, which is in contrast to results obtained in the rat model with acute EAE.

Nevertheless, NA:GLA clearly reduced the intensity of neurological deficits during both acute and relapsing phases.

This study allowed us to determine that NA:GLA was efficient in both models: acute EAE in the rat and chronic-relapsing EAE in the mouse.

EXAMPLE 9

Fatty Acid Compositions of Animal Brain Lipids From Biological Evaluations

Upon termination of certain biological evaluations, rat or mice brains were extracted and the fatty acid composition of total polar lipids from rat/mouse brain was determined.

The aim of these investigations was to determine whether nervonic acid levels within the brain were enhanced following treatment with the nervonic acid derivatives of the invention.

Biological material was sent for analysis to Dr J. Hendersen at the University of Stirling, Institute of Aquaculture, Scotland. Analyses were carried out on two batches of experiments (detailed respectively in Example 6 and Example 7). Results are detailed below.

Results (a) Rat Brain Analyses After NA:DHA/NA:GLA Treatments

Table 17 shows the nervonic acid (NA) content in total polar lipid from rat brain; these animals had been inoculated with acute EAE.

TABLE 17

Nervonic acid composition of total polar lipid from rat brain

| Treatment | Individual values (weight %) | | | | | | | Mean |
|---|---|---|---|---|---|---|---|---|
| | 1 | 2 | 3 | 4 | 5 | 6 | 7 | |
| Normal | 1.6 | 1.7 | 1.0 | 1.8 | 1.6 | — | — | 1.6 ± 0.3 |
| Undosed | 1.2 | 1.4 | 1.2 | 1.7 | 1.5 | 1.3 | — | 1.4 ± 0.2 |
| Vehicle | 1.7 | 1.7 | 1.8 | 1.3 | 1.7 | — | — | 1.7 ± 0.2 |
| NA-DHA (95%) | 1.4 | 1.3 | 1.5 | 1.1 | 1.1 | 1.7 | 1.7 | 1.4 ± 0.2 |
| NA-GLA (low dose) | 2.2 | 2.1 | 2.1 | 2.0 | — | — | — | 2.1 ± 0.1 |
| NA-GLA (high dose) | 2.3 | 2.2 | 1.6 | — | — | — | — | 2.0 ± 0.3 |

Analyses show NA:DHA treatment did not enhance the NA levels in rat brain lipids compared to normal, undosed and vehicle treated animals.

However, there is a marked increase of NA levels in brain lipids after treatment with NA:GLA, at both low and high doses.

(b) Mouse Brain Analyses After NA:NA/NA:GLA Treatments

Table 18 shows the nervonic acid (NA) content in total polar lipid from mouse brain; these animals had been inoculated with chronic-relapsing EAE (CREAE).

TABLE 18

Nervonic acid composition of total polar lipid from mouse brain

| Treatment | Individual values (weight %) | | | | | | | | | | Mean |
|---|---|---|---|---|---|---|---|---|---|---|---|
| | 1 | 2 | 3 | 4 | 5 | 6 | 7 | 8 | 9 | 10 | |
| Undosed | 1.4 | 1.6 | 1.5 | 1.3 | 1.4 | 1.3 | 1.3 | 1.4 | 1.1 | 1.4 | 1.4 ± 0.1 |
| Vehicle | 1.3 | 1.3 | 1.5 | 1.3 | 1.4 | 1.1 | 1.2 | 1.2 | 1.4 | 1.5 | 1.3 ± 0.1 |
| NA:GLA | 1.5 | 1.5 | 1.7 | 1.2 | 1.4 | 1.7 | 1.9 | 2.5 | 1.8 | 2.0 | 1.7 ± 0.4 |
| NA:NA | 2.1 | 2.0 | 2.0 | 1.8 | 2.1 | 1.4 | 2.4 | 1.5 | 1.7 | — | 1.9 ± 0.3 |

Analyses show undosed and vehicle treated mouse brains have a similar level of NA in their lipids. In contrast, NA:GLA and NA:NA show an enhancement of the NA levels in brain lipids, which is even greater for NA:NA treated animals.

Conclusions

Though both DHA and GLA go through the blood-brain barrier, results obtained from brain analyses clearly confirm that these two fatty acids act differently in the form of propane-1,3-diol derivatives: contrary to treatment with NA:DHA, treatment with NA:GLA results in an augmentation of NA level in brain lipids, which may mean NA crosses the blood-brain barrier in the form of NA:GLA.

It is also noteworthy that the greatest increase of NA level in brain lipids triggered by the administration of these derivatives came from NA:NA treated mice, which demonstrates the importance of the propane-1,3-diol unit in the structure of the compound to cross the blood-brain barrier.

Finally, results obtained so far lead us to the conclusion that NA:GLA, which showed activity in both rat and mouse models with, respectively, acute and chronic-relapsing EAE, possesses anti-inflammatory properties and is able to raise the nervonic acid content in brain lipids.

EXAMPLE A

Tablet

| In one tablet | |
| --- | --- |
| Active ingredient | 5.0 mg |
| Lactose | 82.0 mg |
| Starch | 10.0 mg |
| Povidone | 2.0 mg |
| Magnesium stearate | 1.0 mg |

The active ingredient, lactose and starch, are mixed together. The powders are granulated using a solution of povidone in purified water. The granules are dried, the magnesium stearate added and the mixture compressed to produce tablets, 100 mg per tablet.

EXAMPLE B

Ointment Composition

| | |
| --- | --- |
| Active ingredient | 1.0 mg |
| White soft paraffin | to 100.0 g |

The active ingredient is dispersed in a small volume of the vehicle and then incorporated into the bulk of the vehicle to produce a smooth, homogeneous product. Collapsible metal tubes are then filled with the dispersion.

EXAMPLE C

Topical Cream Composition

| | |
| --- | --- |
| Active ingredient | 1.0 g |
| Polawax GP 200 | 20.0 g |
| Lanolin Anhydrous | 2.0 g |
| White Beeswax | 2.5 g |
| Methyl hydroxybenzoate | 0.1 g |
| Distilled Water | to 100.0 g |

The polawax, beeswax and lanolin are heated together at 60° C. A solution of methyl hydroxybenzoate is added and homogenisation is achieved using high speed stirring. The temperature is reduced to 50° C. The active ingredient is then added and dispersed. The composition is allowed to cool with slow-speed stirring.

EXAMPLE D

Topical Lotion Composition

| | |
| --- | --- |
| Active ingredient | 1.0 g |
| Sorbitan monolaurate | 0.6 g |
| Polysorbate 20 ™ | 0.6 g |
| Cetostearyl alcohol | 1.2 g |
| Glycerin | 8.0 g |
| Methyl hydroxybenzoate | 0.2 g |
| Purified water B.P. | to 100.00 ml |

The methyl hydroxybenzoate and glycerin are dissolved in 70 ml of the water at 75°. The sorbitan monolaurate, Polysorbate 20™ and cetostearyl alcohol are melted together at 75° and added to the aqueous solution. The resulting emulsion is homogenised, allowed to cool with continuous stirring and the active ingredient is added as a suspension in the remaining water. The suspension is stirred until homogenised.

EXAMPLE E

Capsule Composition

A capsule is prepared by filling a two-piece hard gelatin capsule with 50 mg of active ingredient, 110 mg of lactose, 32 mg of talc and 8 mg of magnesium stearate.

EXAMPLE F

Eye Drop Composition

| | |
| --- | --- |
| Active ingredient | 0.5 g |
| Methyl hydroxybenzoate | 0.01 g |
| Propyl hydroxybenzoate | 0.04 g |
| Purified water B.P. | to 100.00 ml |

The methyl and propyl hydroxybenzoates are dissolved in 70 ml purified water and the resulting solution is allowed to cool. The active ingredient is added and the solution is sterilised by filtration through a membrane filter (0.22 $\mu$m pore size) and packed into suitable sterile containers.

EXAMPLE G

Composition for Administration by Inhalation

For an aerosol container with a capacity of 15–20 ml: active ingredient (10 mg) is mixed with 0.2–0.2% of a lubricating agent, such as Polysorbate 85™ or oleic acid or a mixture thereof, in a propellant, such as Freon™, preferably in a combination of 1,2-dichloroethene and difluorochloromethane, and the mixture is put into an appropriate aerosol container adapted for inhalation administration.

EXAMPLE H

Composition for Administration by Inhalation (Alcoholic Solution)

For an aerosol container with a capacity of 15–20 ml: active ingredient (10 mg) is dissolved in ethanol (6–8 ml), 0.1–0.2% of a lubricating agent is added, such as Polysorbate 85™, and dispersed in a propellant, such as Freon™, preferably in a combination of 1,2-dichloroethene and difluorochloramethane, and the mixture is put into an appropriate aerosol container adapted for nasal or oral inhalation administration.

EXAMPLE I

Injectable Parenteral Composition

An injection is prepared by stirring 1.5% by weight of active ingredient in propylene glycol and water. The solution is sterilised by filtration.

EXAMPLE J

Oral Composition

An oral composition is prepared by mixing 10 parts of active ingredient (NA:NA and/or NA:GLA) with 90 parts of ethyl oleate, resulting in 10% dilution of the lipid in ethyl oleate.

What is claimed is:

1. A compound of formula (I):

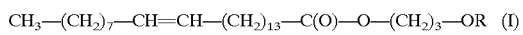

$$CH_3-(CH_2)_7-CH=CH-(CH_2)_{13}-C(O)-O-(CH_2)_3-OR \quad (I)$$

wherein R is a compound selected from the group consisting of hydrogen (H) and a residue of a carboxylic acid; and salts of the compound where R is H; and bioprecursors, prodrugs and hydrates thereof.

2. A compound according to claim 1, wherein R has from 1 to 26 carbon atoms, and is selected from straight-chained or branched-chained, saturated and unsaturated.

3. A compound according to claim 1, wherein the carboxylic acid is straight-chained and is selected from the group consisting of mono- and poly-unsaturated fatty acids.

4. A compound according to claim 1, wherein R is selected from the group consisting of H and residues of $C_{18}$ to $C_{24}$ mono- and poly-unsaturated fatty acids, having from 1 to 6 carbon-carbon double bonds.

5. A compound according to claim 1, wherein R is a compound selected from the group consisting of H and residues of nervonic acid (24:1(n–9)), docosahexaenoic acid (22:6(n–3)) and gamma-linolenic acid (18:3(n–6)), where x in (n–x) indicates the position of the first double bond with respect to the terminal methyl group of the fatty acid.

6. A compound selected from the group consisting of:
   1-(z-15-tetracosenoyloxy)-3-hydroxypropane;
   1-(z-15-tetracosenoyloxy)-3-(z,z,z-6,9,12-octadecatrienoyloxy)propane (hereinafter referred to as NA:GLA);
   1-(z-15-tetracosenoyloxy)-3-(z,-4,7,10,13,16,19-docosahexaenoyloxy)propane (hereinafter referred to as NA:DHA); and
   1,3-di-(z-15-tetracosenoyloxy)propane (hereinafter referred to as NA:NA).

7. A method for the preparation of a compound according to claim 1, comprising:
   (a) reacting a reactive derivative of nervonic acid with propane-1,3-diol in the presence of a base to form a compound of formula (IA):

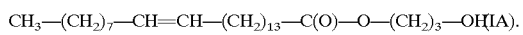

$$CH_3-(CH_2)_7-CH=CH-(CH_2)_{13}-C(O)-O-(CH_2)_3-OH \quad (IA).$$

8. A method for the preparation of a compound according to claim 1, comprising:
   (a) reacting an acid chloride of nervonic acid $CH_3-(CH_2)_7-CH=CH-(CH_2)_{13}-COCl$ with propane-1,3-diol in the presence of a base.

9. A method for the preparation of a compound according to claim 6, comprising:
   (a) reacting a reactive derivative of nervonic acid with propane-1,3-diol in the presence of a base to form a compound of formula (IA):

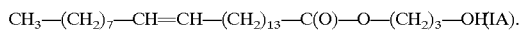

$$CH_3-(CH_2)_7-CH=CH-(CH_2)_{13}-C(O)-O-(CH_2)_3-OH \quad (IA).$$

10. A method for the preparation of a compound according to claim 6, comprising:
    (a) reacting an acid chloride of nervonic acid $CH_3-(CH_2)_7-CH=CH-(CH_2)_{13}-COCl$ with propane-1,3-diol in the presence of a base.

11. A pharmaceutical composition comprising a non-toxic, effective amount of a compound according to claim 1, wherein R is other than H, and a pharmaceutically acceptable carrier therefor.

12. A composition according to claim 11, wherein the carrier comprises ethyl oleate.

13. A composition according to claim 11, wherein the compound is selected from the group consisting of NA:NA, NA:GLA and NA:DHA.

14. A composition according to claim 11, wherein the compound is NA:NA and the carrier is ethyl oleate.

15. A method for preparing a composition according to claim 11, comprising bringing the compound, wherein R is other than H, into association with a pharmaceutically acceptable carrier therefor.

16. A method for the treatment or prevention of an inflammatory condition in a mammal, comprising administering to said mammal of an effective, anti-inflammatory amount of a compound as defined in claim 1.

17. A method according to claim 16, wherein the condition is selected from the group consisting of rheumatoid arthritis, rheumatoid spondylitis, osteroarthritis, gouty arthritis and other arthritic conditions; inflamed joints; eczema and other inflammatory skin conditions; inflammatory eye conditions; conjunctivitis; pyresis; the reduction of tissue necrosis in chronic inflammation; the suppression of tissue rejection following transplant surgery; Crohn's disease; and ulcerative colitis.

18. A method for the treatment or prevention of a condition associated with an immunoregulatory defect in a mammal, comprising administering to said mammal of an effective, immunomodulatory amount of a compound as defined in claim 1.

19. A method according to claim 18, wherein the condition is selected from the group consisting of systemic lupus erythematosis; multiple sclerosis; myasthenia gravis; progressive systemic sclerosis; atopic dermatitis; hyperimmunoglobin E; hepatitis B antigen negative chronic active hepatitis; Hashimoto's thyroiditis; familial Mediterranean fever; Grave's disease; autoimmune haemolytic anaemia; primary biliary cirrhosis; inflammatory bowel disease; and other conditions wherein the immune system is compromised, disabled or dysfunctional.

20. A method for the preparation of a compound according to claim 7, further comprising:
    (b) reacting the compound of formula (IA) thereby prepared with the corresponding carboxylic acid of formula $R^1$—H to form a compound of formula (IB):

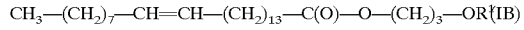

$$CH_3-(CH_2)_7-CH=CH-(CH_2)_{13}-C(O)-O-(CH_2)_3-OR^1 \quad (IB)$$

wherein $R^1$ is a residue of a carboxylic acid; and, optionally, forming a bioprecursor, prodrug or hydrate thereof.

21. A method for the preparation of a compound according to claim 8, further comprising:
    (b) reacting the compound thereby prepared with the corresponding carboxylic acid of formula $R^1$—H to form a compound of formula (IB):

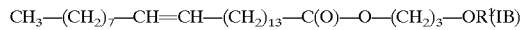

$$CH_3-(CH_2)_7-CH=CH-(CH_2)_{13}-C(O)-O-(CH_2)_3-OR^1 \quad (IB)$$

wherein $R^1$ is a residue of a carboxylic acid; and, optionally, forming a bioprecursor, prodrug or hydrate thereof.

22. A method for the preparation of a compound according to claim 9, further comprising:
    (b) reacting, in the presence of hypophosphorous acid, optionally with heating to reflux under an inert atmosphere, the compound of formula (IA) thereby prepared with the corresponding carboxylic acid of formula $R^1$—H to form a compound of formula (IB):

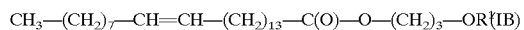

$$CH_3-(CH_2)_7-CH=CH-(CH_2)_{13}-C(O)-O-(CH_2)_3-OR^1 \quad (IB)$$

wherein $R^1$ is a residue of a carboxylic acid; and, optionally, forming a bioprecursor, prodrug or hydrate thereof.

23. A method for the preparation of a compound according to claim 10, further comprising:
   (b) reacting, in the presence of hypophosphorous acid, optionally with heating to reflux under an inert atmosphere, the compound thereby prepared with the corresponding carboxylic acid of formula $R^1$—H to form a compound of formula (IB):

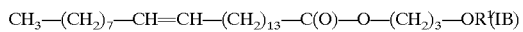

wherein $R^1$ is a residue of a carboxylic acid; and, optionally, forming a bioprecursor, prodrug or hydrate thereof.

24. A method according to claim 19, wherein the condition is selected from the group consisting of AIDS and diseases associated with viral infections.

25. A method for the preparation of a compound according to claim 9, further comprising:
   (b) reacting the compound of formula (IA) thereby prepared with the corresponding carboxylic acid of formula $R^1$—H to form a compound of formula (IB):

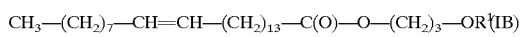

wherein $R^1$ is a residue of a carboxylic acid; and, optionally, forming a bioprecursor, prodrug or hydrate thereof.

26. A method for the preparation of a compound according to claim 10, further comprising:
   (b) reacting the compound thereby prepared with the corresponding carboxylic acid of formula $R^1$—H to form a compound of formula (IB):

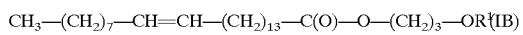

wherein $R^1$ is a residue of a carboxylic acid; and, optionally, forming a bioprecursor, prodrug or hydrate thereof.

27. A method for the preparation of a compound according to claim 7, further comprising:
   (b) reacting, in the presence of hypophosphorous acid, optionally with heating to reflux under an inert atmosphere, the compound of formula (IA) thereby prepared with the corresponding carboxylic acid of formula $R^1$—H to form a compound of formula (IB):

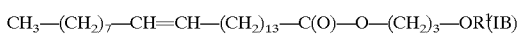

wherein $R^1$ is a residue of a carboxylic acid; and, optionally, forming a bioprecursor, prodrug or hydrate thereof.

28. A method for the preparation of a compound according to claim 8, further comprising;
   (b) reacting, in the presence of hypophosphorous acid, optionally with heating to reflux under an inert atmosphere, the compound thereby prepared with the corresponding carboxylic acid of formula $R^1$—H to form a compound of formula (IB):

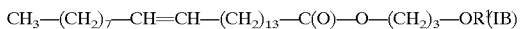

wherein $R^1$ is a residue of a carboxylic acid; and, optionally, forming a bioprecursor, prodrug or hydrate thereof.

29. The method according to claim 19, wherein the condition is HIV.

* * * * *